(12) United States Patent
Kondo

(10) Patent No.: US 11,432,711 B2
(45) Date of Patent: Sep. 6, 2022

(54) ENDOSCOPE

(71) Applicant: OLYMPUS CORPORATION, Hachioji (JP)

(72) Inventor: Toyohiro Kondo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 322 days.

(21) Appl. No.: 16/864,369

(22) Filed: May 1, 2020

(65) Prior Publication Data

US 2020/0253463 A1 Aug. 13, 2020

Related U.S. Application Data

(63) Continuation of application No. PCT/JP2018/035704, filed on Sep. 26, 2018.

(30) Foreign Application Priority Data

Dec. 21, 2017 (JP) .............................. JP2017-244778

(51) Int. Cl.
*A61B 1/00* (2006.01)
*A61B 1/04* (2006.01)
*A61B 1/06* (2006.01)
*G02B 23/24* (2006.01)

(52) U.S. Cl.
CPC .......... *A61B 1/041* (2013.01); *A61B 1/00197* (2013.01); *A61B 1/0684* (2013.01); *G02B 23/243* (2013.01)

(58) Field of Classification Search
CPC ... A61B 1/041; A61B 1/00197; A61B 1/0684; A61B 1/00174; A61B 1/00188; G02B 23/243; G02B 13/02
See application file for complete search history.

(56) References Cited

U.S. PATENT DOCUMENTS

| | | | |
|---|---|---|---|
| 7,153,259 B2 | 12/2006 | Matsuzawa et al. | |
| 7,473,218 B2 | 1/2009 | Segawa et al. | |
| 7,505,802 B2 | 3/2009 | Yoshino | |

(Continued)

FOREIGN PATENT DOCUMENTS

| JP | 2004065575 A | 3/2004 |
|---|---|---|
| JP | 2005080713 A | 3/2005 |

(Continued)

OTHER PUBLICATIONS

International Search Report (ISR) (and English language translation thereof) dated Dec. 25, 2018, issued in International Application No. PCT/JP2018/035704.

(Continued)

*Primary Examiner* — Timothy J Neal
*Assistant Examiner* — Sung Ham
(74) *Attorney, Agent, or Firm* — Holtz, Holtz & Volek PC

(57) ABSTRACT

An endoscope includes an objective optical system, an illuminator having a light-emitting region and the illuminator disposed at a position different from the objective optical system, and a dome-shaped transparent cover transparent in a range of field of view and sealing the object side of the objective optical system and the illuminator. The following Conditional Expressions (1) and (2) are satisfied: $0.5 < \theta/\omega < 0.95$ (1), $(-0.13 \times LP + 0.86 \times DR) < DL < 0.95 \times DR$ (2).

2 Claims, 4 Drawing Sheets

(56) References Cited

U.S. PATENT DOCUMENTS

| | | |
|---|---|---|
| 7,585,275 B2 | 9/2009 | Kubota et al. |
| 7,837,614 B2 | 11/2010 | Segawa et al. |
| 7,854,700 B2 | 12/2010 | Orihara |
| 7,892,164 B2 | 2/2011 | Segawa et al. |
| 7,955,276 B2 | 6/2011 | Yoshino |
| 10,517,468 B2 | 12/2019 | Segawa |
| 2003/0171653 A1* | 9/2003 | Yokoi .................... A61B 1/041 600/179 |
| 2004/0027459 A1 | 2/2004 | Segawa et al. |
| 2005/0054901 A1* | 3/2005 | Yoshino ............. G02B 23/2423 600/176 |
| 2005/0054902 A1* | 3/2005 | Konno ............... G02B 23/2423 600/176 |
| 2005/0124858 A1 | 6/2005 | Matsuzawa et al. |
| 2006/0030752 A1* | 2/2006 | Orihara ................. A61B 1/041 600/407 |
| 2006/0170328 A1 | 8/2006 | Kubota et al. |
| 2007/0055105 A1 | 3/2007 | Matsuzawa et al. |
| 2007/0219435 A1 | 9/2007 | Segawa et al. |
| 2008/0146877 A1 | 6/2008 | Matsuzawa et al. |
| 2008/0167528 A1 | 7/2008 | Segawa et al. |
| 2009/0018398 A1 | 1/2009 | Segawa et al. |
| 2009/0099416 A1 | 4/2009 | Yoshino |
| 2010/0016672 A1 | 1/2010 | Segawa et al. |
| 2012/0016199 A1* | 1/2012 | Baba .................... A61B 1/0607 600/109 |
| 2012/0022327 A1* | 1/2012 | Baba .................. A61B 1/00096 600/109 |
| 2017/0164820 A1 | 6/2017 | Segawa |
| 2018/0307010 A1* | 10/2018 | Amanai ................ G02B 13/06 |

FOREIGN PATENT DOCUMENTS

| | | |
|---|---|---|
| JP | 2005080790 A | 3/2005 |
| JP | 2006043115 A | 2/2006 |
| JP | 2006255247 A | 9/2006 |
| JP | 2008272439 A | 11/2008 |
| WO | 2007125918 A1 | 11/2007 |
| WO | 2016167102 A1 | 10/2016 |

OTHER PUBLICATIONS

Written Opinion dated Dec. 25, 2018, issued in International Application No. PCT/JP2018/035704.

International Preliminary Report on Patentability (IPRP) (and English language translation thereof) dated Jul. 2, 2020 issued in counterpart International Application No. PCT/JP2018/035704.

* cited by examiner

ENDOSCOPE

CROSS-REFERENCE TO RELATED APPLICATION

The present application is a continuation application of PCT/JP2018/035704 filed on Sep. 26, 2018 which is based upon and claims the benefit of priority from Japanese Patent Application No. 2017-244778 filed on Dec. 21, 2017; the entire contents of which are incorporated herein by reference.

BACKGROUND

Technical Field

The disclosure relates to an endoscope.

Description of the Related Art

Conventionally, as a capsule endoscope, there is a known example in which an objective optical system, an illumination unit, an image sensor, a transmitting device, and the like are disposed in a capsule in the form of a tablet, and the object side of these is sealed by a hemispherical cover member (hereinafter referred to as "dome-shaped transparent cover") that is transparent in the range of field of view. In the capsule endoscope configured in this manner, an image in the body captured on the light-receiving surface of the image sensor through the dome-shaped transparent cover and the objective optical system is converted into a signal and transmitted to the outside of the body through the transmitting device. The image received by an external receiving device is displayed on a display device and used for examination.

In the capsule endoscope of this type, part of illumination light emitted from the illumination unit is reflected by the inner surface of the dome-shaped transparent cover and is incident as unnecessary light on the pupil of the objective optical system to cause flare. In order to prevent flare due to reflection by the inner surface of the dome-shaped transparent cover, for example, the arrangements disclosed in Japanese Unexamined Patent Publication No. 2006-43115 and WO2007/125918 are proposed.

SUMMARY

An endoscope according to at least some embodiments includes:
an objective optical system;
an illuminator t having a light-emitting region and the illuminator disposed at a position different from the objective optical system; and a dome-shaped transparent cover transparent in a range of field of view and sealing an object side of the objective optical system and the illuminator, wherein the following Conditional Expressions (1) and (2) are satisfied:

$$0.5 < \theta/\omega < 0.95 \quad (1)$$

$$(-0.13 \times LP + 0.86 \times DR) < DL < 0.95 \times DR \quad (2)$$

where
ω is a half angle of view of the objective optical system,
θ is an angle formed by a straight line and an optical axis of the objective optical system when an intersection point of a light ray at the half angle of view and an inner surface of the dome-shaped transparent cover is connected to a spherical core position of the dome-shaped transparent cover by the straight line,
LP is a distance from an entrance pupil position of the objective optical system to the light-emitting region,
DR is a radius of curvature of the inner surface of the dome-shaped transparent cover, and
DL is a distance from the inner surface of the dome-shaped transparent cover to the entrance pupil position of the objective optical system.

DETAILED DESCRIPTION

An endoscope according to an embodiment, for example, a capsule endoscope 100 will be described in detail below based on the drawings. It should be noted that the present disclosure is not limited by the embodiment.

Figure 1:
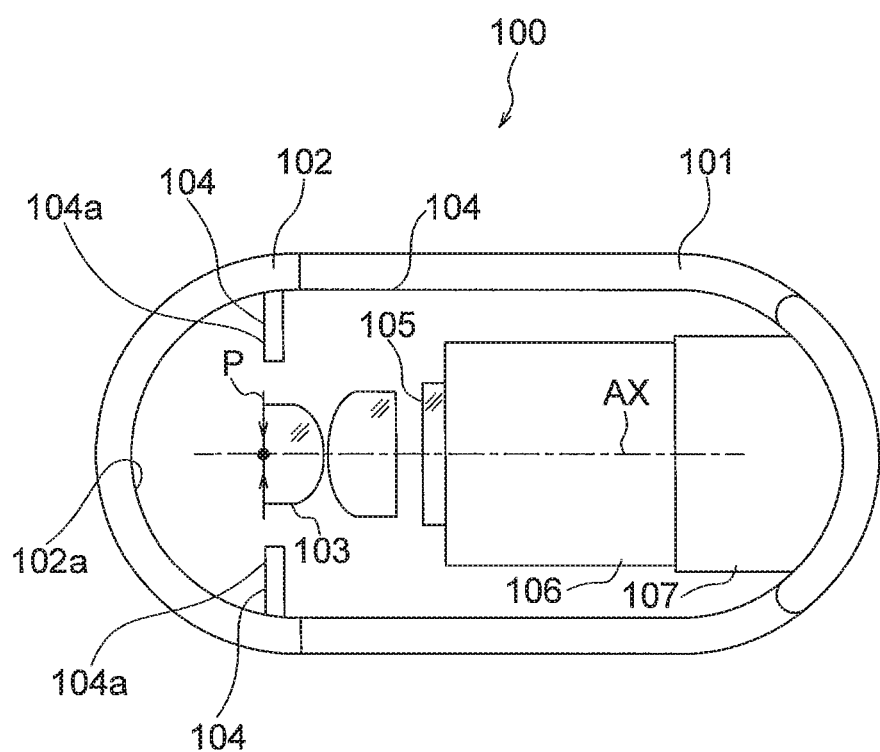
FIG. 1 is a diagram illustrating an overall arrangement of a capsule endoscope according to an embodiment.

FIG. 1 is a diagram illustrating an overall arrangement of a capsule endoscope according to an embodiment. The capsule endoscope 100 includes a capsule cover 101 and a dome-shaped transparent cover 102. An outer casing of the capsule endoscope 100 is formed with the capsule cover 101 and the dome-shaped transparent cover 102.

In the interior of the capsule endoscope 100, an objective optical system 103 and an illumination unit 104 disposed at a position different from the objective optical system 103 are disposed. It is possible to use, for example, an LED having a light-emitting region 104a as the illumination unit 104.

The dome-shaped transparent cover 102 seals the object side of the objective optical system 103 and the illumination unit 104 and is formed of a transparent material in the range of field of view.

The capsule cover 101 includes a substantially cylindrical center portion and a substantially bowl-shaped bottom portion. The dome-shaped transparent cover 102 is disposed at a position opposed to the substantially bowl-shaped bottom portion with the center portion interposed therebetween. The dome-shaped transparent cover 102 is formed with a dome-shaped (substantially bowl-shaped) transparent member. The capsule cover 101 and the dome-shaped transparent cover 102 are connected to each other in a watertight manner.

In the interior of the capsule endoscope 100, the objective optical system 103, the illumination unit 104, an image sensor 105, a drive control unit 106, and a signal processing unit 107 are disposed. The dome-shaped transparent cover 102 is disposed at a position where it covers the front surfaces of both of the objective optical system 103 and the illumination unit 104 at the same time. Although not illustrated, a power receiving unit and a transmitting unit are provided in the interior of the capsule endoscope 100.

Illumination light is emitted from the illumination unit 104. The illumination light passes through the dome-shaped transparent cover 102 and illuminates an object (not illustrated). Light from the object is incident on the objective optical system 103. An optical image of the object is formed at an image position by the objective optical system 103.

The optical image is picked up by the image sensor 105. The drive and the control of the image sensor 105 are performed by the drive control unit 106. Furthermore, an output signal from the image sensor 105 is processed by the signal processing unit 107 as necessary.

The capsule endoscope 100 satisfies the following Conditional Expressions (1) and (2):

$$0.5 < \theta/\omega < 0.95 \qquad (1)$$

$$(-0.13 \times LP + 0.86 \times DR) < DL < 0.95 \times DR \qquad (2)$$

where

ω is the half angle of view of the objective optical system,

θ is the angle formed by a straight line and the optical axis of the objective optical system when the intersection point of a light ray at the half angle of view and the inner surface of the dome-shaped transparent cover is connected to the spherical core position of the dome-shaped transparent cover by the straight line, LP is the distance from the entrance pupil position of the objective optical system to the light-emitting region, DR is the radius of curvature of the inner surface of the dome-shaped transparent cover, and DL is the distance from the inner surface of the dome-shaped transparent cover to the entrance pupil position of the objective optical system.

Figure 2A:
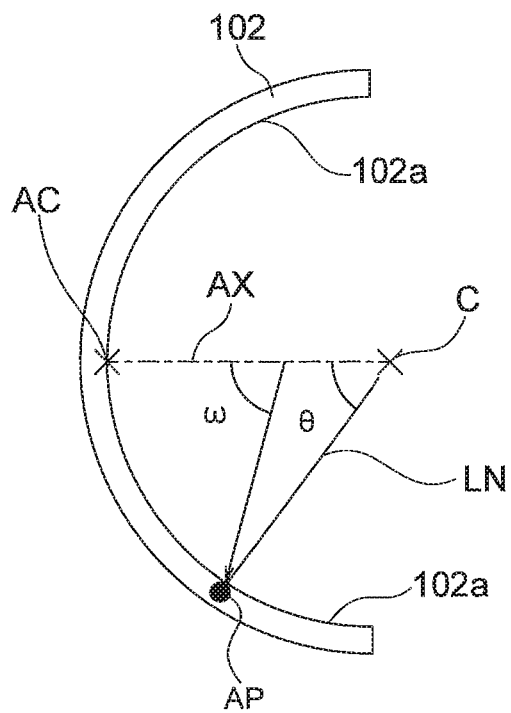
FIGS. 2A and 2B are diagrams illustrating parameters in the present embodiment.
Figure 2B:
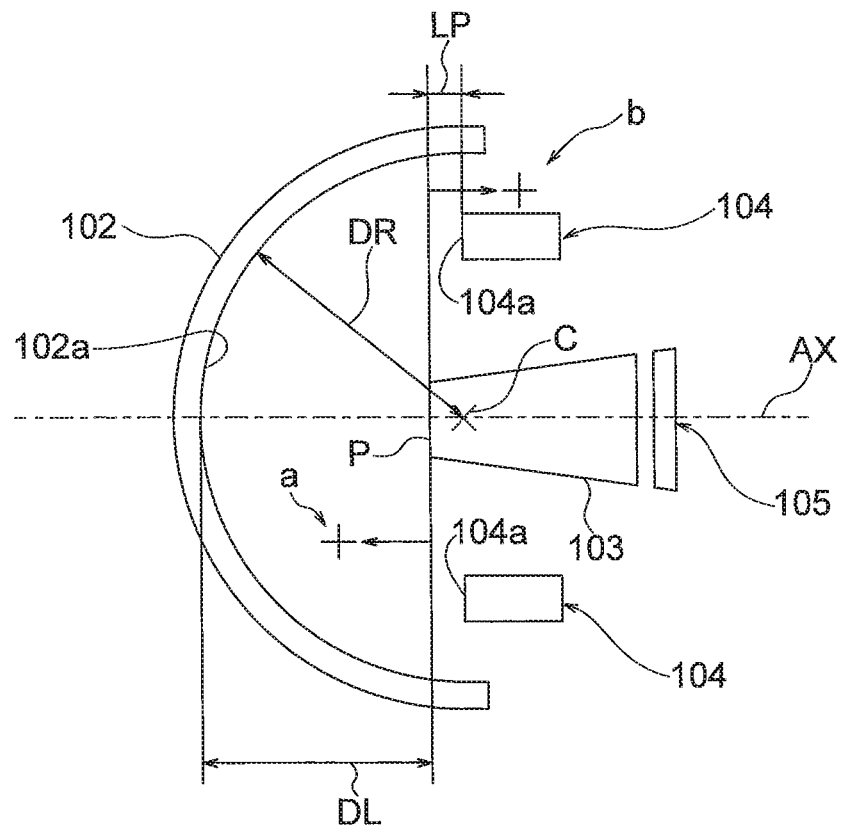

Referring to FIGS. 2A and 2B, the parameters in Conditional Expressions (1) and (2) are described. As illustrated in FIG. 2A, ω is the half angle of view of the objective optical system 103 (see FIG. 1). θ is the angle formed by straight line LN and optical axis AX of the objective optical system 103 (see FIG. 1) when intersection point AP of a light ray at the half angle of view ω and the inner surface 102a of the dome-shaped transparent cover 102 is connected to the spherical core position C of the dome-shaped transparent cover 102 by straight line LN.

Referring to FIG. 2B, the parameters are described. FIG. 2B is a diagram schematically illustrating an arrangement in the vicinity of the dome-shaped transparent cover 102 and the objective optical system 103 of the capsule endoscope. LP is the distance from the position of the entrance pupil P of the objective optical system 103 to the light-emitting region 104a of the LED. LP is positive (+) in direction b away from the dome-shaped transparent cover 102. DR is the radius of curvature of the inner surface 102a of the dome-shaped transparent cover 102. DL is the distance from the inner surface 102a of the dome-shaped transparent cover 102 to the position of the entrance pupil P of the objective optical system 103. DL is positive (+) in direction a closer to the dome-shaped transparent cover 102.

Figure 4A:
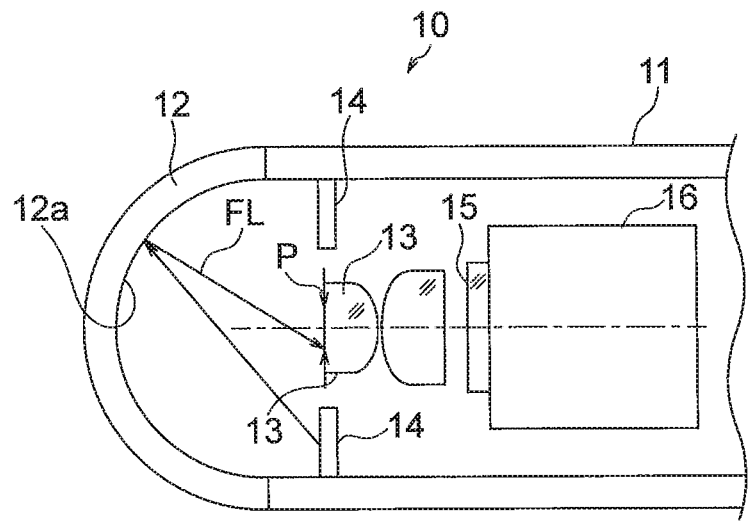
FIGS. 4A, 4B, and 4C are diagrams each illustrating occurrence of flare in a capsule endoscope.
Figure 4B:
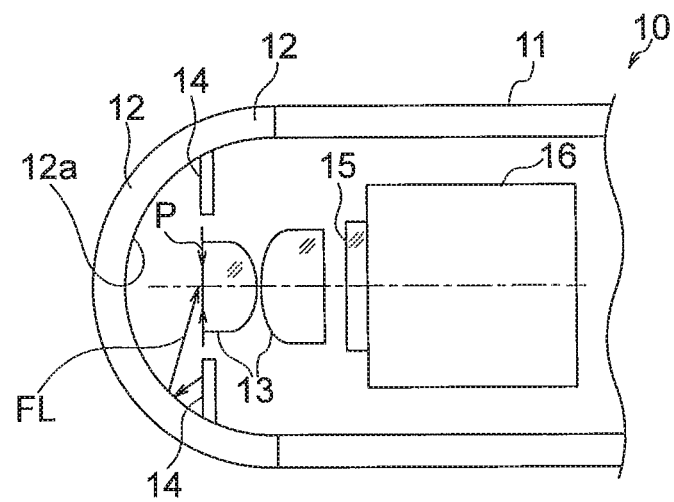
Figure 4C:
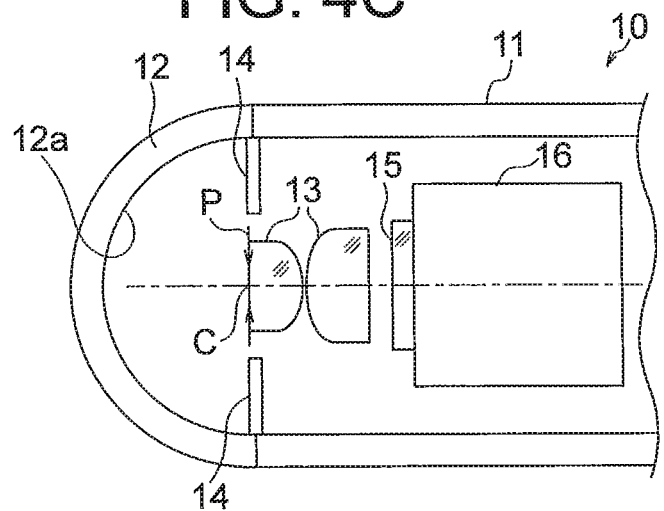

Next, referring to FIGS. 4A, 4B, and 4C, occurrence of flare in a conventional capsule endoscope is described. In FIGS. 4A, 4B, and 4C, a capsule endoscope 10 of a conventional technique includes a capsule cover 11 and a dome-shaped transparent cover 12.

In the interior of the capsule endoscope 10, an objective optical system 13 and an illumination unit 14 disposed at a position different from the objective optical system 13 are disposed. It is possible to use an LED as the illumination unit 14.

The dome-shaped transparent cover 12 seals the object side of the objective optical system 13 and the illumination unit 14 and is formed of a transparent material in the range of field of view.

In the interior of the capsule endoscope 10, the objective optical system 13, the illumination unit 14, an image sensor 15, a drive control unit 16, and a signal processing unit (not illustrated) are disposed. The dome-shaped transparent cover 12 is disposed at a position where it covers the front surfaces of both of the objective optical system 13 and the illumination unit 14 at the same time. Although not illustrated, a power receiving unit and a transmitting unit are provided in the interior of the capsule endoscope 10.

Illumination light is emitted from the illumination unit 14. The illumination light passes through the dome-shaped transparent cover 12 and illuminates an object (not illustrated). Light from the object is incident on the objective optical system 13. An optical image of the object is formed at an image position by the objective optical system 13.

FIG. 4A illustrates an arrangement in which the objective optical system 13 and the illumination unit 14 are disposed at a position farther away from the dome-shaped transparent cover 12. Part of illumination light from the illumination unit 14 is reflected by the inner surface 12a of the dome-shaped transparent cover 12. Part FL of the reflected illumination light is incident on the entrance pupil P of the objective optical system 13. Consequently, flare occurs. Such flare is likely to occur due to variation in position of the dome-shaped transparent cover 12 and variation in position of the illumination unit 14.

FIG. 4B illustrates an arrangement in which the objective optical system 13 and the illumination unit 14 are disposed at a position closer to the dome-shaped transparent cover 12. Part of illumination light from the illumination unit 14 is reflected by the inner surface 12a of the dome-shaped transparent cover 12. Part FL of the reflected illumination light is incident on the entrance pupil P of the objective optical system 13. Consequently, flare occurs.

FIG. 4C illustrates an arrangement in which the position of the entrance pupil P of the objective optical system 13 is substantially matched with the spherical core position C of the inner surface 12a of the dome-shaped transparent cover 12. In this arrangement, flare of single reflection by the inner surface 12a does not occur. However, to obtain the arrangement illustrated in FIG. 4C, trial-and-error position adjustment is necessary for the positional relation between the dome-shaped transparent cover 12 and the illumination unit 14 in a manufacturing process of the capsule endoscope 10.

In the present embodiment, it is possible to prevent flare easily by satisfying the following Conditional Expressions (1) and (2):

$$0.5 < \theta/\omega < 0.95 \qquad (1)$$

$$(-0.13 \times LP + 0.86 \times DR) < DL < 0.95 \times DR \qquad (2)$$

Figure 3A:
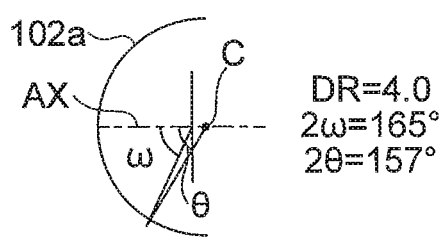
FIGS. 3A, 3B, 3C, and 3D are diagrams illustrating parameters in examples of the present disclosure.
Figure 3B:
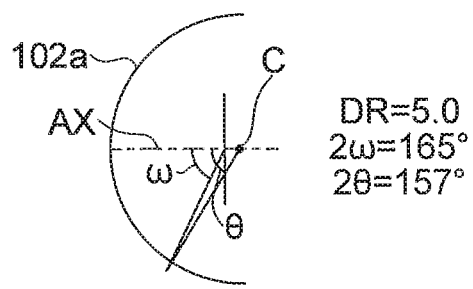

FIG. 3A is a schematic diagram illustrating an arrangement in which the objective optical system 103 and the illumination unit 104 are disposed at a position farthest away from the dome-shaped transparent cover 102 in an example of θ/ω=0.95 and DR=4.0. FIG. 3B is a schematic diagram illustrating an arrangement in which the objective optical system 103 and the illumination unit 104 are disposed at a position farthest away from the dome-shaped transparent cover 102 in an example of θ/ω=0.95 and DR=5.0.

Figure 3C:
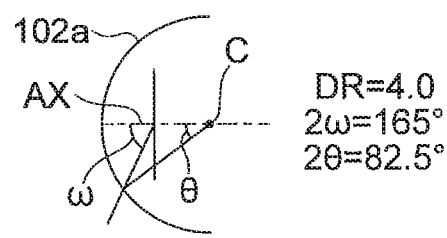
Figure 3D:
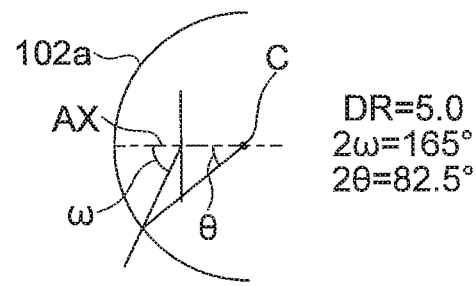

FIG. 3C is a schematic diagram illustrating an arrangement in which the objective optical system 103 and the illumination unit 104 are disposed at a position closest to the dome-shaped transparent cover 102 in an example of θ/ω=0.5 and DR=4.0. FIG. 3D is a schematic diagram illustrating an arrangement in which the objective optical system 103 and the illumination unit 104 are disposed at a position closest to the dome-shaped transparent cover 102 in an example of θ/ω=0.5 and DR=5.0.

Figure 3E:
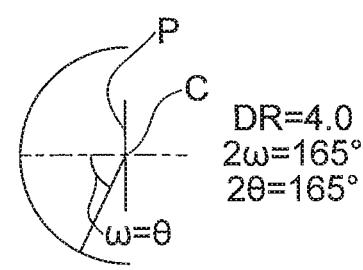
FIGS. 3E and 3F are diagrams illustrating parameters in a conventional technique.
Figure 3F:
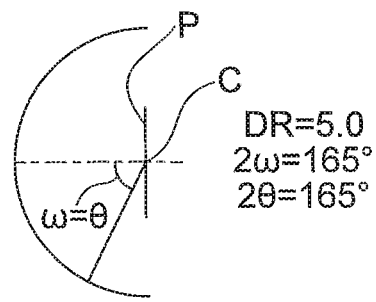

For reference, FIG. 3E is a schematic diagram illustrating an arrangement in a state in which the spherical core position C of the dome-shaped transparent cover 102 matches the entrance pupil P, with DR=4.0. FIG. 3F is a schematic diagram illustrating an arrangement in a state in which the spherical core position C of the dome-shaped transparent cover 102 matches the entrance pupil P, with DR=5.0.

The corresponding values in Numerical Value Example 1 regarding Conditional Expressions (1) and (2) are shown in the following Tables 1, 2, and 3. In the following tables, "upper limit" and "lower limit" indicate the upper limit value and the lower limit value, respectively, allowable as values of parameters.

TABLE 1

| | | |
|---|---|---|
| Angle of view (2ω) | | 140-165 |
| LED light distribution angle (°) | | 140-180 |
| DR (mm) | | 5.0 |
| LP (mm) | 0.0 | 0.4 |

| | Lower limit | Upper limit | Lower limit | Upper limit |
|---|---|---|---|---|
| DL allowable range (mm) | 4.3 | 5.36 | 3.8 | 5.4 |
| DL standardization | 0.86 | 1.07 | 0.76 | 1.08 |

TABLE 2

| (a) | (b) | (c) |
|---|---|---|
| 0.00 | 4.30 | 5.00 |
| 0.05 | 4.20 | 5.00 |
| 0.10 | 4.20 | 5.00 |
| 0.15 | 4.10 | 5.00 |
| 0.20 | 4.10 | 5.00 |
| 0.25 | 4.00 | 5.00 |
| 0.30 | 3.90 | 5.00 |
| 0.35 | 3.90 | 5.00 |
| 0.40 | 3.80 | 5.00 |

(a) LED position
(b) allowable DL lower limit value
(c) DR

TABLE 3

Normalize DR to 1

| (a) | (b) | (c) | (d) | (e) |
|---|---|---|---|---|
| 0.00 | 0.86 | 1.00 | 0.95 | 0.86 |
| 0.01 | 0.84 | 1.00 | 0.95 | 0.85 |
| 0.02 | 0.84 | 1.00 | 0.95 | 0.83 |
| 0.03 | 0.82 | 1.00 | 0.95 | 0.82 |
| 0.04 | 0.82 | 1.00 | 0.95 | 0.81 |
| 0.05 | 0.80 | 1.00 | 0.95 | 0.80 |
| 0.06 | 0.78 | 1.00 | 0.95 | 0.78 |
| 0.07 | 0.78 | 1.00 | 0.95 | 0.77 |
| 0.08 | 0.76 | 1.00 | 0.95 | 0.76 |

(a) LED position
(b) allowable DL lower limit value
(c) DR
(d) DL = 0.95
(e) DL = −1.3 × LP + 0.86 × DR The corresponding values in Numerical Value Example 2 regarding Conditional Expressions (1) and (2) are shown in the following Tables 4, 5, and 6.

TABLE 4

| | | |
|---|---|---|
| Angle of view (2ω) | | 140-165 |
| LED light distribution angle (°) | | 140-180 |
| DR (mm) | | 4.5 |
| LP (mm) | 0.0 | 0.4 |

| | Lower limit | Upper limit | Lower limit | Upper limit |
|---|---|---|---|---|
| DL allowable range (mm) | 3.85 | 4.6 | 3.35 | 4.7 |
| DL standardization | 0.86 | 1.02 | 0.74 | 1.04 |

TABLE 5

| (a) | (b) | (c) |
|---|---|---|
| 0.00 | 3.85 | 4.50 |
| 0.05 | 3.79 | 4.50 |
| 0.10 | 3.73 | 4.50 |
| 0.15 | 3.66 | 4.50 |
| 0.20 | 3.60 | 4.50 |
| 0.25 | 3.54 | 4.50 |
| 0.30 | 3.48 | 4.50 |
| 0.35 | 3.41 | 4.50 |
| 0.40 | 3.35 | 4.50 |

(a) LED position
(b) Permissible DL lower limit value
(c) DR

TABLE 6

Normalize DR to 1

| (a) | (b) | (c) | (d) | (e) |
|---|---|---|---|---|
| 0.00 | 0.86 | 1.00 | 0.95 | 0.86 |
| 0.01 | 0.84 | 1.00 | 0.95 | 0.85 |
| 0.02 | 0.83 | 1.00 | 0.95 | 0.83 |
| 0.03 | 0.81 | 1.00 | 0.95 | 0.82 |
| 0.04 | 0.80 | 1.00 | 0.95 | 0.80 |
| 0.06 | 0.79 | 1.00 | 0.95 | 0.79 |
| 0.07 | 0.77 | 1.00 | 0.95 | 0.77 |
| 0.08 | 0.76 | 1.00 | 0.95 | 0.76 |
| 0.09 | 0.74 | 1.00 | 0.95 | 0.74 |

(a) LED position
(b) allowable DL lower limit value
(c) DR
(d) DL = 0.95
(e) DL = −1.3 × LP + 0.86 × DR The corresponding values in Numerical Value Example 3 regarding Conditional Expressions (1) and (2) are shown in the following Tables 7, 8 and 9.

TABLE 7

| Angle of view (2ω) | | 140-165 | | |
|---|---|---|---|---|
| LED light distribution angle (°) | | 140-180 | | |
| DR (mm) | | 4.0 | | |
| LP (mm) | 0.0 | | 0.4 | |
| | Lower limit | Upper limit | Lower limit | Upper limit |
| DL allowable range (mm) | 3.45 | 4.1 | 2.95 | 4.1 |
| DL standardization | 0.86 | 1.03 | 0.74 | 1.03 |

TABLE 8

| (a) | (b) | (c) |
|---|---|---|
| 0.00 | 3.45 | 4.00 |
| 0.05 | 3.39 | 4.00 |
| 0.10 | 3.33 | 4.00 |
| 0.15 | 3.26 | 4.00 |
| 0.20 | 3.20 | 4.00 |
| 0.25 | 3.14 | 4.00 |
| 0.30 | 3.08 | 4.00 |
| 0.35 | 3.01 | 4.00 |
| 0.40 | 2.95 | 4.00 |

(a) LED position
(b) allowable DL lower limit value
(c) DR

TABLE 9

| Normalize DR to 1 | | | | |
|---|---|---|---|---|
| (a) | (b) | (c) | (d) | (e) |
| 0.00 | 0.86 | 1.00 | 0.95 | 0.86 |
| 0.01 | 0.85 | 1.00 | 0.95 | 0.84 |
| 0.03 | 0.83 | 1.00 | 0.95 | 0.83 |
| 0.04 | 0.82 | 1.00 | 0.95 | 0.81 |
| 0.05 | 0.80 | 1.00 | 0.95 | 0.80 |
| 0.06 | 0.78 | 1.00 | 0.95 | 0.78 |
| 0.08 | 0.77 | 1.00 | 0.95 | 0.76 |
| 0.09 | 0.75 | 1.00 | 0.95 | 0.75 |
| 0.10 | 0.74 | 1.00 | 0.95 | 0.73 |

(a) LED position
(b) allowable DL lower limit value
(c) DR
(d) DL = 0.95
(e) DL = −1.3 × LP + 0.86 × DR The capsule endoscope and the endoscope described above may simultaneously satisfy a plurality of arrangements. Doing so is preferable to obtain a favorable capsule endoscope and the endoscope. Combinations of favorable arrangements are optional. For each conditional expression, only the upper limit value or the lower limit value of a more limited numerical range of the conditional expression may be limited.

Although a variety of embodiments of the present disclosure have been described above, the present disclosure is not limited only to those embodiments, and embodiments configured by combining the configurations of those embodiments as appropriate without departing from the spirit of the disclosure fall within the scope of the disclosure.

In this way, the present disclosure is not limited to a capsule endoscope.

As described above, the disclosure is advantageous for an endoscope, in particular, a capsule endoscope that can prevent flare without depending on trial-and-error position adjustment for the positional relation between the dome-shaped transparent cover and the illumination unit.

The present disclosure achieves an effect of providing an endoscope capable of preventing flare without depending on trial-and-error position adjustment for the positional relation between a dome-shaped transparent cover and an illumination unit.

What is claimed is:

1. An endoscope comprising:
   an objective optical system;
   an illuminator having a light-emitting region and the illuminator disposed at a position different from the objective optical system; and
   a dome-shaped transparent cover transparent in a range of field of view and sealing an object side of the objective optical system and the illuminator, wherein
   the following Conditional Expressions (1) and (2) are satisfied:

$$0.5 < \theta/\omega < 0.95 \quad (1)$$

$$(-0.13 \times LP + 0.86 \times DR) < DL < 0.95 \times DR \quad (2)$$

where
   ω is a half angle of view of the objective optical system,
   θ is an angle formed by a straight line and an optical axis of the objective optical system when an intersection point of a light ray at the half angle of view and an inner surface of the dome-shaped transparent cover is connected to a spherical core position of the dome-shaped transparent cover by the straight line,
   LP is a distance from an entrance pupil position of the objective optical system to the light-emitting region,
   DR is a radius of curvature of the inner surface of the dome-shaped transparent cover, and
   DL is a distance from the inner surface of the dome-shaped transparent cover to the entrance pupil position of the objective optical system on the optical axis.

2. The endoscope according to claim 1, wherein the endoscope is a capsule endoscope.

* * * * *